US012757849B2

(12) United States Patent
McNeil

(10) Patent No.: US 12,757,849 B2
(45) Date of Patent: Oct. 13, 2026

(54) WHEAT VARIETY R14000248#58

(71) Applicant: Syngenta Crop Protection AG, Basel (CH)

(72) Inventor: Sarah Denise McNeil, Manhattan, KS (US)

(73) Assignee: Syngenta Crop Protection AG, Basel (CH)

( * ) Notice: Subject to any disclaimer, the term of this patent is extended or adjusted under 35 U.S.C. 154(b) by 176 days.

(21) Appl. No.: 18/363,028

(22) Filed: Aug. 1, 2023

(65) Prior Publication Data

US 2024/0315190 A1 Sep. 26, 2024

Related U.S. Application Data

(60) Provisional application No. 63/453,777, filed on Mar. 22, 2023.

(51) Int. Cl.
*A01H 6/46* (2018.01)
*A01H 5/10* (2018.01)

(52) U.S. Cl.
CPC ............. *A01H 6/4678* (2018.05); *A01H 5/10* (2013.01)

(58) Field of Classification Search
CPC .................................................... A01H 6/4678
See application file for complete search history.

(56) References Cited

U.S. PATENT DOCUMENTS

2021/0169034 A1* 6/2021 Perry ........................ A01H 5/10

OTHER PUBLICATIONS

Großkinsky et al Journal of Experimental Botany vol. 66, No. 18, pp. 5429-54404 (Year: 2015).*
Haun et al Plant Physiology vol. 155, pp. 645-655 (Year: 2011).*
Minnetonka Minn., “Syngenta Introduces Two New High-Yielding Agripro Brand Winter Wheat Varieties to Plains Growers,” Syngenta, Jul. 19, 2016, 4 pages.
US PVP Certificate No. 200600239, issued Dec. 6, 2006, 15 pages.

* cited by examiner

*Primary Examiner* — David H Kruse
(74) *Attorney, Agent, or Firm* — Destiny Davenport

(57) ABSTRACT

The present invention provides wheat variety R14000248 #58, and derivatives and hybrids thereof. The present invention further provides methods of use of wheat variety R14000248 #58, its derivates, and hybrids, e.g., in breeding.

10 Claims, No Drawings

WHEAT VARIETY R14000248#58

CROSS REFERENCE TO RELATED APPLICATIONS

This application claims benefit of U.S. Provisional application No. 63/453,777, filed on Mar. 22, 2023, the contents of which are incorporated herein by reference in their entirety.

FIELD OF THE INVENTION

The present invention relates to the field of wheat breeding and development. Specifically, the present invention provides a wheat variety designated R14000248 #58, as well as its seed, cells, germplasm, plant parts, derivatives and progeny (including hybrids), and its use in a breeding program.

BACKGROUND OF THE INVENTION

Wheat (particularly *Triticum aestivum L.* and *Triticum turgidum L.*) is a cereal plant and is a worldwide food source as well as a source of raw materials for many other products. Wheat may be classified into six different market classes. Five of these, including common wheat, hard red winter, hard red spring, soft red winter, and white, belong to the species *Triticum aestivum* L., and the sixth, durum, belongs to the species *Triticum turgidum* L. Wheat may be used to produce a variety of products, including, but not limited to, grain, flour, baked goods, cereals, crackers, pasta, beverages, livestock feed, biofuel, straw, construction materials, and starches. The hard wheat classes are generally milled into flour used for breads while the soft wheat classes are generally milled into flour used for pastries and crackers. Wheat starch is used in the food and paper industries as laundry starches, among other products.

Wheat plants are naturally self-pollinating. Self-pollination for several generations produces homozygosity at almost all gene loci, forming a uniform population of true breeding progeny, known as inbreds. Hybrids are developed by crossing two homozygous inbreds to produce heterozygous gene loci in hybrid plants and seeds. In this process, one inbred is emasculated (e.g., using cytoplasmic male sterility) and the pollen from the other inbred pollinates the emasculated inbred. This emasculated inbred produces the hybrid seed, F1. The hybrid seed that is produced is heterozygous.

Such heterozygosity in hybrids generally results in robust and vigorous plants. Inbred plants on the other hand are substantially homozygous, generally rendering them less vigorous. Inbred seed can be difficult to produce due to such decreased vigor. However, when two inbred lines are crossed, the resulting hybrid plant generally shows greatly increased vigor and seed yield compared to open pollinated, segregating wheat plants. An important consequence of the homozygosity and homogeneity of inbred wheat lines is that all hybrid seed and plants produced from any cross of two such lines will be essentially the same. Thus, the use of inbreds allows for the production of hybrid seed that can be readily reproduced.

There are numerous stages in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The aim is to combine in a single variety an improved combination of desirable traits from the parental germplasm. These important traits may include, for example, higher yield, resistance to diseases, fungus, bacteria and insects, better stems and roots, tolerance to drought and heat, improved nutritional quality, and better agronomic characteristics.

The ultimate objective of commercial wheat breeding programs is to produce high yield, agronomically sound plants that perform well in wheat growing regions, such as a variety of this invention.

SUMMARY OF THE INVENTION

The disclosure relates to wheat variety R14000248 #58 and related compositions and methods of use and production thereof.

Accordingly, in some embodiments, the disclosure provides a seed of wheat variety R14000248 #58. In some embodiments, the disclosure provides a plant of wheat variety R14000248 #58. In some embodiments, the disclosure provides a plant part of wheat variety R14000248 #58. In some embodiments, the disclosure provides a seed produced by such plant. In some embodiments, a wheat plant is provided having essentially all (or all) of the physiological and morphological characteristics of a plant of wheat variety R14000248 #58 and further comprising an (i.e., at least one) additional trait, optionally wherein the additional trait is selected from the group consisting of increased drought tolerance, male sterility or restoration of male fertility, modified carbohydrate metabolism, modified amino acid or protein metabolism, modified fatty acid metabolism, altered starch, herbicide resistance, insect resistance, nematode resistance, and disease resistance. In some embodiments, the additional trait is conferred by introducing a transgene (e.g., by introgression or transformation), by introducing a quantitative trait locus (e.g., by introgression), or by genome editing (e.g., by genome editing the plant or by introgression of a genome edited trait). In some embodiments, the disclosure provides a converted seed, plant, plant part or plant cell of wheat variety R14000248 #58, wherein the converted seed, plant, plant part or plant cell comprises a locus conversion, and wherein the plant or a plant grown from the converted seed, plant part or plant cell comprises the locus conversion and otherwise comprises essentially all (or all) of the physiological and morphological characteristics of the seed, plant, plant part or plant cell of wheat variety R14000248 #58 when grown under the same environmental conditions.

In some embodiments, the disclosure provides a method of producing a genetic marker profile comprising extracting nucleic acids from the seed of wheat variety R14000248 #58 or the plant germinated from said seed and genotyping said nucleic acids at one or more genetic loci, thereby producing a genetic marker profile. In some embodiments, the method further comprises selecting the seed or plant based on the genetic marker profile and using said seed or plant in a plant breeding method. In some embodiments, the disclosure provides a method of plant breeding comprising a) isolating nucleic acids from the seed of wheat variety R14000248 #58 or a plant germinated from said seed, b) identifying one or more polymorphisms from the isolated nucleic acids, and c) selecting said seed or a plant obtained from said seed having said one or more polymorphisms, wherein the seed or plant is used in a plant breeding method. In some embodiments, the disclosure provides a process of introducing an (i.e., at least one) additional trait into a wheat plant comprising: (a)

crossing a plant of wheat variety R14000248 #58 with a plant of another wheat variety that comprises an (i.e., at least one) additional trait to produce hybrid progeny plants, (b) selecting one or more hybrid progeny plants that have the additional trait to produce selected hybrid progeny plant(s); (c) crossing the selected progeny plant(s) with the plant of wheat variety R14000248 #58 to produce backcross progeny plants; (d) selecting for one or more backcross progeny plants that have the additional trait to produce selected backcross progeny plant(s); and (e) repeating steps (c) and (d) a sufficient number of times (e.g., two or more times) to produce one or more backcross progeny plants that comprise the additional trait and all of the physiological and morphological characteristics of the plant of wheat variety R14000248 #58 when grown in the same environmental conditions. In some embodiments, the disclosure provides a plant produced by the process. In some embodiments, the disclosure provides a method for developing a second wheat variety in a wheat plant breeding program, comprising applying plant breeding techniques wherein said techniques comprise recurrent selection, backcrossing, pedigree breeding, marker enhanced selection, haploid/double haploid production, or transformation to the wheat plant of wheat variety R14000248 #58, wherein application of said techniques results in development of a second wheat variety. In some embodiments, the disclosure provides a method of producing a commodity plant product comprising collecting the commodity plant product from the plant of wheat variety R14000248 #58.

In some embodiments, the disclosure provides a process for producing wheat seed, said process comprising crossing a plant of wheat variety R14000248 #58 with a different wheat plant, and harvesting the seed. In some embodiments, the disclosure provides a F1 wheat seed produced by the process. In some embodiments, the disclosure provides a F1 wheat plant produced by germinating F1 wheat seed. In some embodiments, the disclosure provides a method of producing a genetic marker profile comprising extracting nucleic acids from the F1 wheat seed or a plant germinated from said seed and genotyping said nucleic acids at one or more genetic loci, thereby producing a genetic marker profile. In some embodiments, the method further comprises selecting the seed or plant based on the genetic marker profile and using said seed or plant in a plant breeding method. In some embodiments, the disclosure provides a method of plant breeding comprising a) isolating nucleic acids from the F1 wheat seed or a plant germinated from said seed, b) identifying one or more polymorphisms from the isolated nucleic acids, and c) selecting said seed or a plant obtained from said seed having said one or more polymorphisms, wherein the seed or plant is used in a plant breeding method. In some embodiments, the disclosure provides a method of producing a wheat plant derived from wheat variety R14000248 #58, the method comprising the steps of (a) growing the F1 wheat plant; (b) crossing said plant with itself or a different plant to produce a seed of a progeny plant; (c) repeating step (b) at least one or more times; and (d) growing said progeny plant from said seed and crossing the progeny plant with itself or a different plant to produce a wheat plant derived from wheat variety R14000248 #58. In some embodiments, the disclosure provides a method for developing a second wheat variety in a wheat plant breeding program, comprising applying plant breeding techniques wherein said techniques comprise recurrent selection, backcrossing, pedigree breeding, marker enhanced selection, haploid/double haploid production, or transformation to the F1 wheat plant, wherein application of said techniques results in development of a second wheat variety. In some embodiments, the disclosure provides a method of producing a commodity plant product comprising collecting the commodity plant product from the F1 wheat plant. In some embodiments, the disclosure provides a wheat plant with doubled haploid chromosomes the method comprising: (a) crossing the F1 wheat plant with an inducer wheat plant to produce a progeny with haploid chromosomes; and (b) doubling the haploid chromosomes in the progeny to produce a wheat plant with doubled haploid chromosomes.

Definitions

R14000248 #58 is an elite wheat line originating through cytoplasmic male sterility (CMS) conversion of the public variety POSTROCK, derived through backcrossing. The pedigree for R14000248 #58 is (R2/SY WOLF*)/((PR302/POSTROCK_F1)/POSTROCK).

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

In the description and examples that follow, a number of terms are used. To provide a clear and consistent understanding of the specifications and claims, including the scope to be given such terms, the following definitions are provided.

A, An, The: As used herein, “a,” “an” or “the” can mean one or more than one. For example, a cell can mean a single cell or a multiplicity of cells. When used in conjunction with the word “comprising” or other open language in the claims, the words “a” and “an” denote “one or more.”

And/Or: As used herein, “and/or” refers to and encompasses any and all possible combinations of one or more of the associated listed items, as well as the lack of combinations when interpreted in the alternative (or).

About: The term “about,” as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount. About refers to embodiments or values that include the standard deviation of the mean for a given item being measured.

Allele: Any of one or more alternative forms of a locus or sequence, all of which relate to one trait or characteristic. In a diploid cell or organism, the two alleles of a given locus occupy corresponding loci on a pair of homologous chromosomes. These two sequence alleles correspond to the same locus (i.e., position) on homologous chromosomes.

Aluminum Tolerance Rating: This rating is for tolerance to aluminum (A13+) concentration in soils, mostly expressed in low pH soils with high ppm of aluminum. Agronomic performance under this stress is relative to known tolerant and susceptible lines. Susceptible lines exhibit varying levels of yellowing (chlorosis) and stunting. Each genotype is given a 1 to 9 score based on its tolerance with 1 being 100% tolerant exhibiting no symptoms, 5 being intermediate in reaction with moderate levels of stunting and/or yellowing, and 9 being 100% susceptible and stunted to the point of plant death.

Aphids: Aphid resistance is scored on a scale from 1 to 9; a score of 4 or less indicates resistance. Varieties scored as 1 to 5 appear normal and healthy, with numbers of aphids increasing from none to up to 300 per plant. A score of 7 indicates that there are 301 to 800 aphids per plant and that the plants show slight signs of infestation. A score of 9 indicates severe infestation and stunted plants with severely curled and yellow leaves.

Ash: Ash refers to the mineral material in the flour milled from the wheat.

Auricle: A wheat auricle is a project at the lower end of the leaf-blade. Auricles on wheat are blunt and hairy.

Awn: Awn is intended to mean the elongated needle-like appendages on the flower- and seed-bearing head at the top of the cereal grain plant (e.g., wheat, common wheat, rye). Awns are attached to the lemmas. Lemmas enclose the stamen and the stigma as part of the florets. Florets are grouped in spikelets, which in turn together comprise the head.

Backcrossing: A process in which a breeder repeatedly crosses progeny, for example a first generation hybrid (F1), back to one of the parents of the progeny. Backcrossing can be used to introduce one or more single locus conversions from one genetic background into another. In a backcrossing scheme, the "donor" parent refers to the parental plant with the desired gene or locus to be introduced. The "recipient" parent (used one or more times) or "recurrent" parent (used two or more times) refers to the parental plant into which the gene or locus is being introduced. For example, see Ragot, M. et al. Marker-assisted Backcrossing: A Practical Example, in Techniques et Utilisations des Marqueurs Moleculaires Les Colloques, Vol. 72, pp. 45-56 (1995); and Openshaw et al., Marker-assisted Selection in Backcross Breeding, in Proceedings of the Symposium "Analysis of Molecular Marker Data," pp. 41-43 (1994). The initial cross gives rise to the F1 generation. The term "BC1" refers to the second use of the recurrent parent, "BC2" refers to the third use of the recurrent parent, and so on.

Bacterial leaf Streak: Bacterial leaf streak (BLS) is caused by *Xanthomonas translucens pv. undulosa*. It is an important disease on wheat and herein, it is rated on a 1-9 scale where 1=no disease.

Bake Absorption (Bake Abs.): Measure determined subjectively by test baker representing the optimal dough baking performance. Estimates are obtained from mixograph data.

Baking Quality: The suitability of a wheat variety to produce a particular product. For example, the quality of the protein in the flour may result in differences in bread loaf volume in hard wheat and differences in the spread and surface texture of cookies in soft wheat.

Boot: Boot refers to one of the wheat growth stages. The boot stage begins when the head begins to form inside the flag leaf.

Cell: As used herein, the term cell includes a plant cell, whether isolated, in tissue culture, or incorporated in a plant or plant part.

Coleoptile anthocyanin: The intensity of anthocyanin coloration in wheat coleoptiles 2 to 6 days after germination; visually determined to be Absent, Reddish, Purple, or Mixed.

Cross or Crossed refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant) and use of haploid inducer to form haploid seeds.

Crumb: Crumb refers to the pattern and size of holes inside of a loaf.

Crumb Color: Rating for color of loaf crumb. Scored from 1 to 6, where 1 is excellent.

Crumb Grain: Physical structure of loaf crumb. Scored from 1 to 9, where 1 is excellent.

Crumb Texture: Tactile texture of loaf. Scored from 1 to 6, where 1 is excellent.

Culm: Culm refers to the aerial stem of a wheat plant.

Cultivar and Variety refer to a substantially homozygous wheat line and minor modifications thereof that retains the overall genetics of the wheat line including but not limited to a subline, a locus conversion, a mutation, a transgenic, or a somaclonal variant. Variety or cultivar include seeds, plants, plant parts, and/or seed parts of the instant wheat line.

Disease Resistance: As used herein, the term disease resistance or disease resistant is defined as the ability of plants to restrict the activities of a specified disease, such as a fungus, virus, or bacterium or to endure a specified disease (such as a fungus, virus, or bacterium) or an adverse environmental condition and still perform and produce in spite of this disorder.

Drought tolerance: The relative ability of a wheat plant to develop and yield grain in dry conditions.

Elite Inbred, Elite Line—Wheat plant that is substantially homozygous and which contributes useful agronomic and/or phenotypic qualities when used to produce hybrids that are commercially acceptable.

Emasculate: The removal of plant male sex organs or the inactivation of the organs with a cytoplasmic or nuclear genetic factor or a chemical agent conferring male sterility.

Embryo: The embryo is the small plant contained within a mature seed.

Emergence: The emergence score describes the ability of a seed to emerge from the soil after planting. Each genotype is given a 1 to 9 score based on its percent of emergence. A score of 1 indicates an excellent rate and percent of emergence, an intermediate score of 5 indicates an average rating and a 9 score indicates a very poor rate and percent of emergence.

Enzymes: Molecules which can act as catalysts in biological reactions.

Essentially all of the morphological and physiological characteristics: The characteristics of a plant are recovered that are otherwise present when compared in the same environment, other than occasional variant traits that might arise during backcrossing or direct introduction of a transgene.

F1 Hybrid: The first generation progeny of the cross of two nonisogenic plants.

FDK: *Fusarium* damaged kernels per 30 grams.

Flag leaf: The last leaf produced upon the culm.

Flour Hardness: Hard flour is flour higher in protein content (12-14%) made from hard wheat.

Flour Protein: Protein content of flour as measured by NIR. Typically ranges from 8-13%; analyzed on a 14% moisture basis.

Flour Yield: Total amount of flour (Break & Reduction flour blend) yielded after removal of bran and shorts. Milled on a Brabender Quadrumat Sr. Milling System. Flour yield is calculated to a 14% grain moisture basis.

Gene: A segment of nucleic acid that codes for a protein or functional non-coding RNA and is the basic unit of heredity. A gene can be introduced into the genome of a species from a different species using, e.g., transformation.

Gene Converted (Conversion): Gene conversion or a gene converted plant refers to plants that are developed by backcrossing, transformation, genetic engineering, or mutation, wherein essentially all of the morphological and physiological characteristics of a variety are recovered, in addition to the one or more traits transferred into the variety via the backcrossing technique, transformation, genetic engineering, or mutation. In some specific embodiments, a gene conversion may result from a native gene conversion rather than a transgenic gene conversion.

Gene Silencing: Gene silencing refers to the interruption or suppression of the expression of a gene at the level of transcription or translation.

Genotype: The genetic constitution of a cell or organism.

Glume: The dry protective casings (bracts) of the seed attached to the spikelet in grasses.

Glume blotch: a disease of wheat characterized by small, irregular gray to brown spots or blotches on the glumes, although infections may also occur at the nodes. The disease is caused by the fungus *Stagonosporum nodorum* (may also be referred to as *Septoria nodorum*).

Resistance to this disease is scored on scales that reflect the observed extent of the disease on the leaves of the plant. Rating scales may differ but in general a low number indicates resistance and higher number suggests different levels of susceptibility.

Glume color: The color of the dry protective casings of the seeds or cereal grain; visually determined as White, Yellow, Light Brown, Brown, Red, Purple or Other Specified. Glume Color (GLMCC): Color of glumes prior to pollen shed. The description of the glume color can include, but is not limited to, (1) Red or (2) Green.

Haploid: A cell or organism having one set of the two or more sets of chromosomes in a diploid or polyploid.

Head: As used herein, the term head refers to a group of spikelets at the top of one plant stem. The term spike also refers to the head of a plant located at the top of one plant stem.

Heading stage: The heading stage of wheat begins when the ear emerges from the flag leaf sheath and ends when the entire ear has emerged, measured on a 1-9 relative rating scale where each increment equals one day, where 1=early.

Heading Date: Measured in Julian days, the formation of the spike.

Herbicide Tolerance: As used herein, the term herbicide tolerance or herbicide tolerant is defined as the ability of plants to survive and reproduce after herbicide treatment.

Insect Resistance: As used herein, the term insect resistance or insect resistant is defined as the ability of plants to restrict the activities of or kill a specified insect pest or the ability of plants to endure a specified insect pest and still perform and produce in spite of this insect pest.

Introduce or Introducing (and grammatical equivalents thereof) in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part (e.g., transformation). It also refers to both the natural and artificial transmission of a desired allele, transgene, or combination of desired alleles of a genetic locus or genetic loci, or combination of desired transgenes from one genetic background to another. For example, a desired allele or transgene at a specified locus can be transmitted to at least one progeny via a sexual cross between two parents of the same species, where at least one of the parents has the desired allele or transgene in its genome. Alternatively, for example, transmission of an allele or transgene can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele or transgene can be repeatedly backcrossed to a line having a desired genetic background and selected for the desired allele or transgene, with the result being that the desired allele or transgene becomes fixed in the desired genetic background.

Leaf Rust (1-9 scale; 1=no disease): Leaf Rust is a disease of wheat characterized by pustules that are circular or slightly elliptical, that usually do not coalesce, and contain masses of orange to orange-brown spores. The disease is caused by the fungus *Puccinia recondita f.* sp. *tritici*. Infection sites primarily are found on the upper surfaces of leaves and leaf sheaths, and occasionally on the neck and awns. Resistance to this disease is scored on scales that reflect the observed extent of the disease on the leaves of the plant. Rating scales may differ but in general a low number indicates resistance and higher number suggests different levels of susceptibility Lemma: A lemma refers to an external bract, one of two bracts surrounding the flower in the floret.

Linkage: A phenomenon wherein alleles on the same chromosome tend to not separate during meiosis of homologous chromosomes. Thus, during meiosis this segment of DNA remains unbroken more often than expected by chance.

Linkage Disequilibrium—The tendency of alleles to remain in linked groups when segregating from parents to progeny more often than expected from chance.

Loaf volume: Volume of bread loaf in cubic centimeters (cc). Obtained by rapeseed displacement method.

Locus: A defined segment of DNA. A locus is a position on a genomic sequence that is usually found by a point of reference, for example, the position of a DNA sequence that is a gene, or part of a gene or intergenic region. A locus confers one or more traits such as, for example, male sterility, herbicide tolerance, insect resistance, nematode resistance, disease resistance, modified fatty acid metabolism, modified phytic acid metabolism, modified carbohydrate metabolism or modified protein or amino acid metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Lodging: Lodging is rated on a scale of 1 to 9. A score of 1 indicates erect plants (no lodging). A score of 5 indicates plants are leaning at a 45-degree(s) angle in relation to the ground and a score of 9 indicates plants are lying on the ground. When rating wheat, lodging can also be referred to as standability.

Male Sterility: A condition in which pollen is absent or nonfunctional in flowering plants.

Marker: A readily detectable phenotype or genotype, e.g., detectable via a single nucleotide polymorphism or haplotype.

Maturity: As used herein, the term maturity refers to the stage of plant growth at which the development of the kernels is complete.

Milling Quality: The quantity and color of the flour produced.

Mixograph: Approved method (American Association of Cereal Chemists Method 54-40A) for measuring and recording resistance of a dough to mixing. The mixing curve (mixogram) indicates optimum development time (point of minimum mobility), tolerance to overmixing, and other dough characteristics, and estimates bake absorption.

Mixograph Absorption (Mixo Abs): The amount of water added to the mixograph at which dough development is optimum and as an estimation of the bake absorption. The mixograph absortion is adjusted for flour protein and reported as a percent.

Mixograph Rating: Rating based off the mixograph curve (as a whole) for tolerance, mix time, and curve type. Scored from 1 to 9, where 1 is excellent.

Moisture (%): Percent moisture of grain at harvest.

Near-infrared reflectance: Near-infrared reflectance (NIR) was used to determine protein content of grain and flour based on transmittance or reflectance of near-infrared energy.

Near-infrared reflectance (NIR) spectroscopy: provides a rapid measurement of certain compositional factors of flour sample. Reflectance signal affected by particle size. Used to determine Whole Wheat Protein, Flour Protein, and Flour Hardness.

Peak Time: Time at which dough development is optimum. Reported in Mixograph results in minutes (min).

Peak Height: Determined from Mixograph results as the height of the graph at the middle of the curve at Peak Time. Results reported in centimeters (cm).

Pedigree Distance: Pedigree distance is the relationship among generations based on their ancestral links as evidenced in pedigrees. It may be measured by the distance of the pedigree from a given starting point in the ancestry.

Percent Identity: Percent identity, as used herein, refers to the comparison of the homozygous alleles of two wheat varieties. Percent identity is determined by comparing a statistically significant number of the homozygous alleles of two developed varieties. For example, a percent identity of 90% between wheat variety 1 and wheat variety 2 means that the two varieties have the same allele at 90% of their loci.

Percent Similarity: Percent similarity as used herein refers to the comparison of the homozygous alleles of a wheat variety with another plant, and if the homozygous allele of the wheat variety matches at least one of the alleles from the other plant then they are scored as similar. Percent similarity is determined by comparing a statistically significant number of loci and recording the number of loci with similar alleles as a percentage. A percent similarity of 90% between a wheat variety and another plant means that the wheat variety matches at least one of the alleles of the other plant at 90% of the loci.

Phenotype: The detectable characteristics of a cell or organism, which characteristics are the manifestation of gene expression.

Plant: Means the plant, in any of its stages of life including the seed or the embryo, the cotyledon, the plantlet, the immature or the mature plant, the plant parts, plant protoplasts, plant cells of tissue culture from which wheat plants can be regenerated, plant calli, plant clumps, and plant cells (but only to the extent the genetic makeup of the cell has both paternal and maternal material) that are intact in plants or parts of the plants, such as pollen, anther, nodes, roots, flowers, seeds, pods, leaves, stems, petals and the like.

Plant Appearance: This is a visual rating based on general plant appearance, taking into account all factors of intactness, pest and disease pressure. Various responses include, but are not limited to, (1) Complete plant with healthy appearance; (2) Plants look okay; or (3) Plants are not acceptable.

Plant Height: As used herein, the term plant height is defined as the average height in inches or centimeters of a group of plants, as measured from the ground level to the tip of the head, excluding awns. Height (1-9): 1=short; 4=70 centimeters Plant Part: As used herein, the term plant parts (or reference to "a wheat plant, or a part thereof") includes, but is not limited to, protoplasts, callus, leaves, stems, roots, root tips, anthers, pistils, seed, grain, pericarp, embryo, pollen, ovules, cotyledon, hypocotyl, spike, floret, awn, lemma, shoot, tissue, petiole, cells, and meristematic cells.

Powdery Mildew: Powdery Mildew is a disease of wheat characterized by white to pale gray, fuzzy or powdery colonies of mycelia, and conidia on the upper surfaces of leaves and leaf sheaths (especially on lower leaves), and sometimes on the spikes. The disease is caused by the fungus *Erysiphe graminis f.* sp. *tritici*. Older fungal tissue is yellowish gray. This superficial fungal material can be rubbed off easily with the fingers. Host tissue beneath the fungal material becomes chlorotic or necrotic and, with severe infections, the leaves may die. Eventually, black spherical fruiting structures may develop in the mycelia, and can be seen without magnification. Resistance to this disease is scored on scales that reflect the observed extent of the disease on the leaves of the plant. Rating scales may differ but in general a low number indicates resistance and higher number suggests different levels of susceptibility.

Protein, grain: Percentage protein content of the wheat grain reported as a percentage at 12% moisture basis.

Quantitative Trait Loci (QTL): Quantitative trait loci refer to genetic loci that control to some degree numerically representable traits that are usually continuously distributed.

Rachis: The main axis of the inflorescence, or spike, of wheat and other cereals, to which the spikelets are attached.

Regeneration: The development of a plant from tissue culture.

*Rhizoctonia* Root Rot: a disease of wheat characterized by sharp eyespot lesions that develop on basal leaf sheaths. The disease is caused by the fungus *Rhizoctonia solani*. The lesion margins are dark brown with pale, straw-colored centers and the mycelia often present in the centers of lesions are easily removed by rubbing. Roots can also be affected, usually becoming brown in color and reduced in number. The disease can cause stunting and a reduction in the number of tillers. Resistance to this disease is scored on scales that reflect the observed extent of the disease on the leaf sheaths of the plant and on reduced vigor of the plant. Rating scales may differ but in general a low number indicates resistance and higher number suggests different levels of susceptibility.

Scab or *Fusarium* (scale 1-9; 1=no disease) Head Blight (FHB): Scab or Head Blight a disease of wheat characterized by florets (especially the outer glumes) that become slightly darkened and oily in appearance. The disease is caused by the fungus *Fusarium* which has numerous species. Spores are produced that can give the spike and shriveled, infected kernels a bright pinkish color. Spores can produce a toxin, deoxynivalenol (DON, vomitoxin) which can be measured with a chemical test. Resistance to this disease can be measured in three ways: the extent of the disease on the spikes of the plant, the percent kernels which are visibly shriveled and the amount of deoxynivalenol in the kernels. Rating scales may differ but in general a low number indicates resistance and higher number suggests different levels of susceptibility.

SDS Sedimentation (SEDML): SDS sedimentation (sodium dodecyl sedimentation) test values are a measure of the end-use mixing and handling properties of bread dough and their relation to bread-making quality as a result of the dough's gluten quality. Higher SDS sedimentation levels reflect higher gluten quality.

Self-pollination: The transfer of pollen from the anther to the stigma of the same plant.

*Septoria* Leaf Blotch or Speckled Leaf Blotch: Speckled leaf blotch is a disease of wheat, common wheat and durum wheat characterized by irregularly shaped blotches that are at first yellow and then turn reddish brown with grayish brown dry centers, caused by the rust fungus *Septoria tritici*. Resistance to this disease is scored on scales that reflect the observed extent of the disease on the leaves of the plant. Rating scales may differ but in general a low number indicates resistance and higher number suggests different levels of susceptibility.

Shattering: the detachment of grain from the plant before harvest typically caused by heavy rain, hail, or high winds.

Single Locus Converted (Conversion) Plant: Plants that are developed by backcrossing or by genetic transformation or genome editing to introduce a locus, in which essentially all of the morphological and physiological characteristics of a wheat cultivar are recovered in addition to the characteristics of the locus transferred into the variety. It is understood that once introduced into any wheat plant genome, a locus that is transgenic in origin (transgene), can also be introduced by backcrossing as with any other locus.

Soil Born Mosaic Virus: Soil born mosaic virus is a disease of wheat characterized by mild green to yellow mosaic, yellow-green mottling, dashes, and parallel streaks, most clearly visible on the youngest leaf. Reddish streaking and necrosis at leaf tips sometimes occurs. Stunting can be moderate to severe, depending on the variety. The disease is caused by a virus which is transmitted by a soilborne fungus-like organism, *Polymyxa graminis*, which makes swimming spores that infect the roots of wheat. Resistance to this disease is scored on scales that reflect the observed extent of the disease on the young plants. Rating scales may differ, but in general, a low number indicates resistance and a higher number suggests different levels of susceptibility.

Spike: Spike refers to the head of a plant located at the top of one plant stem.

Stem Rust: Stem Rust is a disease of wheat characterized by pustules containing masses of spores that are dark reddish brown, and may occur on both sides of the leaves, on the stems, and on the spikes. The disease is caused by the fungus *Puccinia graminis f.* sp. *Tritici*. Resistance to this disease is scored on scales that reflect the observed extent of the disease on the leaves of the plant. Rating scales may differ, but in general, a low number indicates resistance and a higher number suggests different levels of susceptibility.

Stripe Rust: Stripe rust is a disease of wheat, common wheat, durum wheat, and barley characterized by elongated rows of yellow spores on the affected parts, caused by a rust fungus, *Puccinia striiformis*. Resistance to this disease is scored on scales that reflect the observed extent of the disease on the leaves of the plant. Rating scales may differ, but in general, a low number indicates resistance, and a higher number suggests different levels of susceptibility.

Substantially Equivalent: A characteristic that, when compared, does not show a statistically significant difference (e.g., p=0.05) from the mean.

Thousand kernel Weight (TKW, in grams): As used herein, the term kernel weight refers to the weight of individual kernels (also called seeds), often reported as the weight of one thousand kernels or "1000 Kernel Weight".

Tolerance (Tol): Measure of dough resistance (tolerance) to overmixing and directly related to quantity and strength of gluten-forming proteins. Calculated based on measurements recorded at the top and bottom of the Mixograph curve at Peak Time, and top and bottom at 3 minutes after Peak Time. The higher the number, the more tolerant the sample.

Wheat Streak Mosaic Virus Rating (also including *Triticum* Mosaic Virus or HiPlains Mosaic Virus): Prevalent in Western Central Plains of North America, symptoms of Wheat Stream Mosaic Virus complex include stunting, yellowing and streaking of leaves potentially up to reduction of stand and sterility of plants. Leaves of plants infected with wheat streak mosaic have a bright yellow streaking. Symptoms are often most severe near the leaf tip. The virus that causes wheat streak mosaic survives in volunteer wheat and is spread by wheat curl mites. The disease is often most severe in areas of a field that are closest to these sources of the disease and mites. Commonly, plants infected with wheat streak mosaic also are infected with High Plains disease and *Triticum* mosaic. The symptoms of these diseases are nearly identical. Disease severity is greater when plants are infected by more than one virus. Each genotype is given a 1 to 9 score based on its tolerance with 1 being 100% tolerant exhibiting no symptoms, 5 being intermediate in reaction with moderate levels of streaking and/or tolerance, and 9 being 100% susceptible with plants being completely stunted and/or chlorotic.

Yield: Refers to the weight of harvested grains per unit area. Corrected to standardized measures for grain moisture (13.5%) and grain weight per volume (60 lbs/bu). Reported in bushels per acre.

DETAILED DESCRIPTION OF THE INVENTION

Hybrid and Inbred Production

Any breeding methods using the wheat variety R14000248 #58, and its progeny are part of this invention. Inbred development can be accomplished by different methods, for example, pedigree selection, backcrossing, recurrent selection, and/or haploid/doubled haploid production. An inbred plant with similar genetic or characteristics to wheat variety R14000248 #58 could be produced by applying double haploid methods to the progeny of a cross between wheat variety R14000248 #58 and a different plant. Double haploid methods produce substantially homozygous plants without repeated backcrossing steps. The haploid/doubled haploid process of developing inbreds starts with the induction of a haploid by using, for example, inducers lines (see, e.g., Liu et al. Plant Biotechnol J. 2020; Extension of the in vivo haploid induction system from diploid maize to hexaploid wheat. 18(2):316-318). Other methods for induction of a haploid include the Y cross method (in which sweet corn pollen is used for pollination), anther culture, and pollen spore techniques. The haploid cell is then at least doubled (e.g., using colchicine), and the at least doubled haploid plant is produced. Methods for producing double haploid wheat are known in the art (see, e.g., Patial et al. 2019; Doubled Haploidy Techniques in Wheat (*Triticum aestivum L.*): An Overview. Proc. Natl. Acad. Sci., India, Sect. B Biol. Sci. 89, 27-41; Tadesse et al. Afr J Biotechnol. 2012. Recent advances and application of doubled haploids in wheat breeding. 11. 10.5897/AJB12.2124 and Humpreys. Advances in Plant Breeding Strategies: Breeding, Biotechnology and Molecular Tools. 2015. pp. 241-290. Springer, Cham. Doubled Haploid Breeding in Cereals. ISBN 978-3-319-22520-3). In some embodiments, a method of producing an wheat plant with at least doubled haploid chromosomes derived from the wheat variety R14000248 #58 the method comprising: (a) crossing a plant, wherein said plant may have one or more traits, with an inducer wheat plant to produce a progeny with haploid chromosomes; and (b) at least doubling the haploid chromosomes in the progeny to produce a wheat plant with at least doubled haploid chromosomes. In some embodiments, the progeny may be for example a cell, seed, embryo or plant. In further embodiments, the wheat plant with at least doubled haploid chromosomes produced by step (b) above is a wheat inbred plant with the characteristics of wheat variety R14000248 #58. In other embodiments, the plant crossed with an inducer in step (a) is a hybrid wheat plant produced by crossing wheat variety R14000248 #58 with a different plant. Sometimes this at least doubled haploid can be used as an inbred but sometimes it is further self-pollinated to finish the inbred development.

Another breeding process is pedigree selection which uses the selection in an F2 population produced from a cross of two genotypes (often elite inbred lines), or selection of progeny of synthetic varieties, open pollinated, composite, or backcrossed populations. Pedigree selection is effective for highly heritable traits but other traits, such as yield, require replicated test crosses at a variety of stages for accurate selection.

The wheat variety and hybrid wheat lines of the present invention can be employed in a variety of breeding methods that can be selected, depending on the mode of reproduction, the trait and/or the condition of the germplasm. Thus, any breeding methods using wheat variety R14000248 #58 or its progeny are part of this invention. Such methods can include, but are not limited to, marker assisted breeding, selection, selfing, backcrossing, hybrid production, and crosses to populations.

All plants and plant cells produced using wheat variety R14000248 #58 are encompassed within the present invention, which also encompasses the wheat variety used in crosses with other, different, wheat varieties to produce corn hybrid seeds and hybrid plants and the grain produced on the hybrid plant. This invention includes progeny plants and plant cells, which upon growth and differentiation produce wheat plants having the physiological and morphological characteristics of the wheat variety R14000248 #58 when grown in the same environmental conditions.

Wheat breeders select for a variety of traits in inbred plants that impact hybrid performance in addition to selecting for acceptable parental traits. Such traits include, but are not limited to, yield potential in hybrid combination, dry down, maturity, grain moisture at harvest, resistance to root lodging, tillering habit, resistance to stalk lodging, grain quality, disease resistance, drought tolerance, insect resistance, nematode resistance, and plant height. Additionally, because hybrid performance may differ in different soil types such as those having low levels of organic matter, clay, sand, black, high pH, or low pH; or in different environments such as wet environments, drought environments, and no tillage conditions, multiple trials testing for agronomic traits may be run to assert hybrid performance across environments. These traits are governed by a complex genetic system that can make selection and breeding of an inbred line extremely difficult. However, even if an inbred, in hybrid combination, has excellent yield (a desired characteristic), it may not be useful for hybrid seed production if the inbred lacks acceptable parental traits, for example, seed size, pollen production, plant height, etc.

The following example is provided to illustrate the difficulty of breeding and developing inbred lines. Two inbreds compared for similarity of 30 traits differ significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. The fact that wheat is polyploid means that the rate of fixation could be even lower and difficult to obtain. Selection of the specific inbred combination is also influenced by the specific selection environment on many of these traits which makes the probability of obtaining this one inbred even more remote. In addition, most traits in the wheat genome are not single dominant genes; they are multi-genetic with additive gene action but not dominant gene action. Thus, the general approach of producing a non-segregating F1 generation and self pollinating to produce an F2 generation that segregates for traits and then selecting progeny from the F2 generation with the desired visual traits does not easily lead to a useful inbred. Great care and breeder expertise must be used in the selection of breeding material to continue to increase yield and enhance desirable agronomic features of inbreds and resultant commercial hybrids.

In one embodiment, a method of producing a plant of this invention is by planting the seed of wheat variety R14000248 #58, which is substantially homozygous, self-pollinating or sib pollinating the resultant plant in isolate environment, and harvesting the resultant seed. The F1 hybrid seed can be produced using two distinct inbreds, the male inbred contributing pollen to the female seed producing parent, the female seed producing parent, on the other hand, is not contributing pollen to the seed. Thus, in some embodiments, a method is provided for producing an hybrid wheat seed by crossing a plant of wheat variety R14000248 #58 with a different wheat plant (e.g., a different inbred line), and harvesting the resultant hybrid wheat seed. A wheat plant of the present invention can act as a male or female part in hybrid production.

A method is also provided for producing wheat seed comprising growing the plant of this invention until seed is produced and harvesting the seed, wherein the harvested seed is inbred or hybrid or haploid seed. Plants and plant parts produced by the seed of this method is also provided herein. Additionally, provided herein is a method of producing hybrid seed wheat from this inbred wheat line and producing hybrid plants and seeds from the hybrid seed wheat of this invention.

Thus, in some embodiments, the invention provides hybrid seed, produced by planting, in pollinating proximity, seeds of wheat variety R14000248 #58 and seeds of another inbred line. The wheat plants resulting from said planting are cultivated; emasculation of one of the inbred lines (i.e., the selected inbred plant) and allowing pollination to occur. Seeds produced by plants of the selected inbred can be harvested. In further embodiments, seeds of wheat variety R14000248 #58 are planted and cultivated. Alternatively, emasculated plants are pollinated with preserved wheat pollen. The seeds produced by wheat variety R14000248 #58 pollinated with the preserved pollen can be harvested. The hybrid seed produced by the hybrid combination of plants of wheat variety R14000248 #58 and plants of another inbred line or produced by the plants of wheat variety R14000248 #58 pollinated by preserved pollen are included in the present invention. This invention further encompasses hybrid plants and plant parts thereof including but not limited to the grain and pollen of the plant grown from this hybrid seed.

In two alternative embodiments, the method is provided for producing an hybrid wheat seed, the method comprising crossing a plant of wheat variety R14000248 #58 with a different wheat variety (e.g., a different inbred line), wherein the pollen of the wheat variety R14000248 #58 pollinates the different wheat variety, or in the alternative the pollen of the different wheat variety pollinates wheat variety R14000248 #58, and the resultant hybrid wheat seed is harvested.

In some embodiments, methods of producing a hybrid described herein involve use of a line that is emasculated. In some embodiments the line is emaculated via cytoplasmic male sterility (CMS). Cytoplasmic male sterility or "CMS" refers to cytoplasmic-based and maternally-inherited male sterility. CMS is total or partial male sterility in plants as the result of specific nuclear and mitochondrial interactions and is maternally inherited via the cytoplasm. One example is the *Triticum timopheevii*-type cytoplasmic male sterility (T-CMS) (see, e.g., Wilson. Wheat Int. Serv. 1962; 14:29-30). In some embodiments, a CMS line is crossed to a line comprising a restorer gene. Methods of creating CMS lines and use of restorer genes are known in the art (see, e.g., Melonek et al., Nat Commun. 2021; 12(1):1036 and PCT Publication Nos. WO2017158128, WO2017158126, WO2017158127, and WO2019086510).

The invention further relates to methods for producing other wheat breeding lines derived from the wheat inbred of this invention by crossing the wheat variety R14000248 #58 with a second wheat plant and growing the progeny seed to yield a wheat variety R14000248 #58-derived wheat plant. Thus, in some embodiments of this invention, a method is provided for producing a wheat plant derived from wheat variety R14000248 #58, the method comprising the steps of: (a) growing a hybrid progeny plant wherein the wheat variety of this invention is a parent (b) crossing the hybrid progeny plant with itself or a different plant to produce a seed of a progeny plant; (c) growing the progeny plant from said seed and crossing the progeny plant with itself or a different plant; and (d) repeating steps (c) for an additional generation to produce a wheat plant derived from wheat variety R14000248 #58. The present invention also provides a wheat seed produced by crossing the plant of this invention with itself or a different wheat plant.

Thus, other aspects of this invention include a method for developing a wheat plant in a wheat plant breeding program, comprising applying plant breeding techniques comprising recurrent selection, backcrossing, pedigree breeding, marker enhanced selection, haploid/double haploid production, or transformation to the wheat plant of this invention, or its parts, wherein application of said techniques results in development of a wheat plant.

Transfer of Additional Traits into Wheat Variety R14000248 #58

A specific location on a chromosome can be referred to as a locus. Trait conversion refers to a variety that has been modified such that the variety retains its physiological and morphological characteristics except for those changed by the introduction of the trait(s). Thus, a variety undergoing an herbicide resistance trait conversion will evidence the additional trait of resisting damage by the herbicide. The variety will after trait conversion have one or more loci with a specific desired trait. Such a variety modification may be through mutant genes, transgenes, genome editing, or native traits. A wheat line and any minor genetic modifications which may include a trait conversion, a mutation, or a variant is a variety.

The use of an inbred wheat plant, such as the inbred of the present invention, as a recurrent parent in a breeding program is a form of backcrossing. Backcrossing is often employed to introduce an additional trait or trait(s), either transgenic or non-transgenic, into a recurrent parent. A plant with a desired trait or locus is crossed into a recurrent wheat parent usually in one or more backcrosses. If markers are employed to assist in selection of progeny that have the desired trait and recurrent parent background genetics, then the number of backcrosses needed to recover the recurrent parent with the desired trait or locus can be relatively few, e.g., two or three. However, 3, 4, 5 or more backcrosses are often required to produce the desired inbred with the gene or locus conversion in place. The number of backcrosses needed for a trait introduction is often linked to the genetics of the line carrying the trait and the recurrent parent and the genetics of the trait. Multigenic traits, recessive alleles and unlinked traits can affect the number of backcrosses that may be necessary to achieve the desired backcross conversion of the inbred.

Basic wheat crossing techniques, as well as other wheat breeding methods, including pedigree breeding, backcross breeding, and bulk breeding, are known in the art (e.g., as described in U.S. Pat. No. 8,809,654). Dominant, single gene traits or traits with obvious phenotypic changes are particularly well managed in backcrossing programs, as are well known in the art. A backcross conversion or locus conversion both refer to a product of a backcrossing program.

A backcrossing program is more complicated when the trait is a recessive gene. A determination of the presence of the recessive gene requires the use of some testing to determine if the trait has been transferred. Use of markers to detect the gene reduces the complexity of trait identification in the progeny. A marker specific for a recessive trait, such as a single nucleotide polymorphism (SNP), can increase the efficiency and speed of tracking the recessive trait within a backcrossing program.

The last backcross generation can be selfed, if necessary, to give pure breeding progeny for the nucleic acid(s) being transferred. The resulting plants generally have essentially all of the morphological and physiological characteristics of the inbred wheat line of interest, in addition to the transferred trait(s) (e.g., one or more gene traits). The exact backcrossing protocol will depend on the trait being altered to determine an appropriate testing protocol.

Thus, in some embodiments, one or more additional traits can be introduced into a plant of this invention using any method known in the art for introducing traits into plants. Nucleotide sequences encoding traits of interest can all be located at the same genomic locus in the donor, non-recurrent parent, and in the case of transgenes, can be part of a single DNA construct integrated into the donor's genome or into additional chromosomes integrated into the donor's genome. Alternatively, if the nucleotide sequences of interest are located at different genomic loci in the donor, non-recurrent parent, backcrossing can be carried out to establish all of the morphological and physiological characteristics of the plant of the invention in addition to the nucleotide sequences encoding the traits of interest in the resulting wheat inbred line.

Accordingly, the present invention provides a method of introducing or introgressing at least one additional trait into wheat variety R14000248 #58, comprising the steps of: (a) crossing a plant grown from the seed of wheat variety R14000248 #58 (which is the recurrent parent), with a donor plant of another wheat line that comprises at least one additional trait to produce F1 plants; (b) selecting F1 plants having the at least one additional trait to produce the selected F1 progeny plants; (c) crossing the F1 plants of (b) with the recurrent parent to produce backcrossed progeny plants having the at least one additional trait; (d) selecting for backcrossed progeny plants that have at least one of the additional traits and physiological and morphological characteristics of wheat inbred line of the recurrent parent to produce selected backcrossed progeny plants; and (e) repeating the crossing of the selected backcrossed progeny to the recurrent parent of step (c) and the selecting of step (d) in succession to produce a plant that comprises at least one additional trait and essentially all of the physiological and morphological characteristics of wheat variety R14000248 #58 when grown in the same environmental conditions (e.g., essentially the recurrent parent having the at least one additional trait).

In some embodiments of this invention, the at least one additional trait comprises the trait of herbicide resistance, insect resistance, nematode resistance, disease resistance, male fertility or sterility, abiotic stress, altered phosphorus content, altered antioxidants, altered essential amino acids, and altered nutritional quality, or any combination thereof.

In some embodiments, the selecting and crossing steps of (e) are repeated at least 3 times in order to produce a plant that comprises the at least one desired trait and essentially all of the physiological and morphological characteristics of the wheat inbred line of the recurrent parent in the present invention when grown under the same environmental conditions (as determined at the 5% significance level). In other embodiments, the selecting and crossing steps of (e) are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to produce a plant that comprises the at least one additional trait and essentially all of the physiological and morphological characteristics of the wheat inbred line of the recurrent parent in the present invention. In other embodiments, the crossing and growing steps of (a) and (b) in step (c) are repeated from 0 to n times (wherein n can be any number) in order to produce a plant that comprises the at least one additional trait and essentially all of the physiological and morphological characteristics of the wheat inbred line of the recurrent parent in the present invention.

Another aspect of the invention provides a wheat plant having essentially all the physiological and morphological characteristics of wheat variety R14000248 #58 and further comprising an additional trait, wherein the additional trait is selected from the group consisting of herbicide resistance, insect resistance, nematode resistance, disease resistance, male fertility or sterility, abiotic stress, altered phosphorus content, altered antioxidants, altered essential amino acids, and altered nutritional quality, or any combination thereof. In some embodiments, the additional trait is conferred by introducing a transgene, introducing a QTL, or by genome editing. Some embodiments of the invention provide a seed produced by the wheat plant having essentially all the physiological and morphological characteristics of wheat variety R14000248 #58 and further comprising an additional trait.

The method of introducing traits as described herein can be done with fewer back crossing events if the trait and/or the genotype of the present invention is selected for or identified through the use of markers. Simple sequence repeats (SSRs or microsatellites), single nucleotide polymorphisms (SNPs) and the like decrease the amount of breeding time required to locate a line with the desired trait or traits and the characteristics of the present invention. Backcrossing in two or even three traits is routinely done with the use of marker assisted breeding techniques and or selection pressure testing. Introduction of transgenes or mutations into a wheat line is known as single gene conversion. More than one gene and, in particular, transgenes and/or mutations that are readily tracked with markers, can be moved during the same "single gene conversion" process. This single gene conversion process results in a line comprising more desired or targeted traits than just the one but still having the characteristics of the plant line of the present invention plus those characteristics added by the desired/targeted traits.

In some aspects, the present invention provides a converted seed, plant, plant part or plant cell of inbred wheat variety R14000248 #58, representative seed of the wheat variety R14000248 #58 having been deposited, wherein the converted seed, plant, plant part or plant cell comprises a locus conversion, and wherein the plant or a plant grown from the converted seed, plant part or plant cell comprises the locus conversion and otherwise comprises essentially all of the physiological and morphological characteristics of wheat variety R14000248 #58 when grown under the same environmental conditions.

A locus conversion refers to plants within a variety that have been modified in a manner that retains the overall genetics of the variety and further comprises one or more loci with a specific desired trait, such as, e.g., male sterility, insect resistance, nematode resistance, disease resistance or herbicide tolerance. Examples of single locus conversions include mutant genes, transgenes and native traits finely mapped to a single locus. One or more locus conversion traits may be introduced into a single wheat variety.

Genetic variants of wheat variety R14000248 #58 that are naturally occurring or created through traditional breeding methods using wheat variety R14000248 #58 are also intended to be within the scope of this invention. In particular embodiments, the invention encompasses plants of this invention and parts thereof further comprising one or more additional traits, in particular, specific, single gene transferred traits. Examples of traits that may be transferred include, but are not limited to, herbicide resistance, insect resistance, nematode resistance, disease resistance, male fertility or sterility, abiotic stress, altered phosphorus content, altered antioxidants, altered essential amino acids, and altered nutritional quality, or other agronomically important traits.

Such traits may be introduced into a plant of this invention from another wheat line or through direct transformation into or mutation (e.g., genome editing) of a plant of this invention. One or more new traits can be transferred to a plant of this invention, or, alternatively, one or more traits of a plant of this invention are altered or substituted. The introduction of the trait(s) into a plant of this invention may be achieved by any method of plant breeding known in the art, for example, pedigree breeding, backcrossing, and the like.

Nucleic Acids for Introduction into Wheat Plants of the Present Invention

As would be appreciated by one of skill in the art, any nucleotide sequence of interest can be introduced into the plants and/or parts thereof of the present invention. Some exemplary nucleotide sequences and traits that may be used with the present invention are provided herein.

Methods and techniques for introducing and/or introgressing a trait or nucleotide sequence into a plant of the present invention through breeding, transformation, site specific insertion, mutation and the like, are well known and understood by those of ordinary skill in the art. Non-limiting examples of such techniques include, but are not limited to, anther culturing, haploid/double haploid production, transformation, irradiation to produce mutations, genome editing, and chemical or biological mutation agents.

Transformation of Wheat Variety R14000248 #58 Plants and/or Parts Thereof

The term transgenic plant refers to a plant having one or more heterologous genetic sequences that are introduced into the genome of a plant (e.g., by a transformation method) and the progeny thereof. With the advent of molecular biological techniques that have allowed the isolation and characterization of nucleic acids that encode specific protein products, scientists in the field of plant biology developed a strong interest in engineering the genome of plants to contain and express foreign nucleic acids, or additional, or modified versions of native or endogenous nucleic acids (perhaps driven by different promoters) in order to alter the traits of a plant in a specific manner. Such foreign, additional and/or modified nucleic acids are referred to herein collectively as “transgenes.” The term “transgene,” as used herein, is not necessarily intended to indicate that the foreign nucleic acid is from a different plant species. For example, the transgene may be a particular allele derived from another wheat line or may be an additional copy of an endogenous gene. Over the last twenty to twenty-five years several methods for producing transgenic plants have been developed. Therefore, in particular embodiments, the present invention also encompasses transformed plants and/or parts thereof (e.g., cells, seeds, anthers, ovules, and the like) of wheat variety R14000248 #58.

Transformation methods are techniques for integrating new nucleotide sequence(s) into the genome of a plant by recombinant nucleic acid technology, rather than by standard breeding practices. However, once a transgene is introduced into plant material and stably integrated, standard breeding practices can be used to move the transgene into other germplasm.

Plant transformation generally involves the construction of an expression vector that will function in plant cells. Such a vector comprises DNA or RNA comprising a nucleic acid under control of, or operatively linked to, a regulatory element (for example, a promoter). The expression vector may contain one or more such operably linked nucleic acid/regulatory element combinations. The vector(s) may be in the form of, for example, a plasmid or a virus, and can be used, alone or in combination with other vectors, to provide transformed wheat plants, using transformation methods as described below to incorporate transgenes into the genetic material of the wheat plant(s).

Any transgene(s) known in the art may be introduced into a wheat plant, tissue, cell or protoplast according to the present invention, e.g., to improve commercial or agronomic traits, herbicide resistance, disease resistance (e.g., to a bacterial fungal or viral disease), insect resistance, nematode resistance, yield enhancement, nutritional quality (e.g., oil starch and protein content or quality), altered reproductive capability (e.g., male sterility), and the like or any combination thereof. Alternatively, a transgene may be introduced for the production of recombinant proteins (e.g., enzymes) or metabolites.

A recombinant nucleic acid molecule of the invention can be introduced into a plant cell in a number of art-recognized ways. Suitable methods of transforming plant cells include microinjection, electroporation, *Agrobacterium*-mediated transformation, direct gene transfer, biolistic transformation, and protoplast transformation/regeneration methods. See, e.g., Hayta et al. Plant Methods. 2019 Oct. 26; 15:121; Hamada et al. Sci Rep. 2017 Sep. 13; 7(1):11443; and Borisjuk et al. Biomed Res Int. 2019; 2019: 6216304).

A vector or nucleic acid construct can comprise leader sequences, transit polypeptides, promoters, terminators, genes or nucleotide sequences of interest, introns, nucleotide sequences encoding genetic markers, etc., and any combination thereof. The nucleotide sequence(s) of the vector or nucleic acid construct can be in sense, antisense, partial antisense, or partial sense orientation in any combination and multiple gene or nucleotide sequence copies can be used. The transgene or nucleotide sequence can come from a plant as well as from a non-plant source (e.g., bacteria, yeast, animals, and viruses).

A vector or nucleic acid construct comprising a transgene that is to be introduced into a plant of this invention can comprise the transgene and/or encoding nucleotide sequence under the control of a promoter appropriate for the expression of the transgene and/or nucleotide sequence at the desired time and/or in the desired tissue or part of the plant. Constitutive or inducible promoters can be used, and are well known in the art. The vector or nucleic acid construct carrying the transgene and/or encoding nucleotide sequence can also comprise other regulatory elements such as, e.g., translation enhancers or termination signals. In some embodiments, the transgene or encoding nucleotide sequence is transcribed and translated into a protein. In other embodiments, the vector or nucleic acid construct can comprise a nucleotide sequence that encodes an antisense RNA, a sense RNA that is not translated or only partially translated, a mRNA, a tRNA, a rRNA and/or a snRNA, as are well known in the art.

In general, methods to transform, modify, edit or alter plant endogenous genomic DNA (e.g., genome editing) include altering the plant native DNA sequence or a pre-existing transgenic sequence including regulatory elements, coding and non-coding sequences. These methods can be used, for example, to target nucleic acids to pre-engineered target recognition sequences in the genome. Such pre-engineered target sequences may be introduced by genome editing or modification. As an example, a genetically modified plant variety is generated using “custom” or engineered endonucleases such as meganucleases produced to modify plant genomes (see e.g., WO 2009/114321; Gao et al. (2010) Plant Journal 1:176-187). Another site-directed engineering method is through the use of zinc finger domain recognition coupled with the restriction properties of restriction enzyme. See e.g., Urnov, et al., (2010) Nat Rev Genet. 11(9):636-46; Shukla, et al., (2009) Nature 459 (7245):437-41. A transcription activator-like (TAL) effector-DNA modifying enzyme (TALE or TALEN) may also used to engineer changes in a plant genome. See e.g., US20110145940, Cermak et al., (2011) Nucleic Acids Res. 39(12) and Boch et al., (2009), Science 326(5959): 1509-12. Site-specific modification of and insertion into plant genomes can also be performed using endonucleases, such as the CRISPR (clustered regularly interspaced short palindromic repeats)/Cas (CRISPR/Cas) system. See e.g., Belhaj et al., (2013), Plant Methods 9: 39; and Bandyopadhyay et al. (2020) Front Plant Sci. 11:584151.

Plant Tissue Culture and Regeneration

Plant cells, which have been transformed by any method known in the art, can also be regenerated to produce intact plants using known techniques. Plant regeneration from cultured protoplasts is described in Evans et al., Handbook of Plant Cell Cultures, Vol. 1: (MacMilan Publishing Co.

New York, 1983); and Vasil I. R. (ed.), Cell Culture and Somatic Cell Genetics of Plants, Acad. Press, Orlando, Vol. I, 1984, and Vol. II, 1986). It is known that practically all plants can be regenerated from cultured cells or tissues.

Means for regeneration vary from species to species of plants, but generally a suspension of transformed protoplasts or a petri plate containing transformed explants is first provided. Callus tissue is formed and shoots may be induced from callus and subsequently root. Alternatively, somatic embryo formation can be induced in the callus tissue. These somatic embryos germinate as natural embryos to form plants. The culture media will generally contain various amino acids and plant hormones, such as auxin and cytokinins. A large number of plants have been shown capable of regeneration from transformed individual cells to obtain transgenic whole plants. Patents and patent publications cited as exemplary for the processes for transforming plant cells and regenerating plants are the following: U.S. Pat. Nos. 4,459,355, 4,536,475, 5,464,763, 5,177,010, 5,187,073, 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253 and 5,405,765; European Patent Nos. EP 267,159, EP 604 662, EP 672 752, EP 442 174, EP 486 233, EP 486 234, EP 539 563 and EP 674 725, and PCT Publication Nos. WO 91/02071 and WO 95/06128.

The use of pollen, cotyledons, zygotic embryos, meristems and ovum as the target tissue for transformation can eliminate or minimize the need for extensive tissue culture work. Generally, cells derived from meristematic tissue are useful. A method of transformation of meristematic cells of cereal is taught in PCT Publication No. WO96/04392. Any number of various cell lines, tissues, calli and plant parts can and have been transformed by those having knowledge in the art. Methods of preparing callus or protoplasts from various plants are well known in the art. Cultures can be initiated from most of the above-identified tissues. The only requirement of the plant material to be transformed is that it can ultimately be used to produce a transformed plant.

Accordingly, in some embodiments, the present invention provides a tissue culture of regenerable cells of wheat variety R14000248 #58, wherein the cells of the tissue culture regenerate plants that express the genotype of wheat variety R14000248 #58. The tissue culture can be but is not limited to tissue culture derived from protoplast, callus, leaf, root, root tip, anther, seed, embryo, pollen, and ovule. In some aspects of this invention, additionally provided is a tissue culture of regenerable cells of hybrid plants produced from wheat variety R14000248 #58 germplasm. A wheat plant regenerated from wheat variety R14000248 #58 or any part thereof is also included in the present invention. The present invention additionally provides regenerated wheat plants that express the genotype of wheat variety R14000248 #58 and/or manifest its phenotype, as well as mutants and/or variants thereof.

Transgenic Plants and/or Parts Thereof of Wheat Variety R14000248 #58

Wheat variety R14000248 #58 and progeny thereof comprising at least one transgene adapted to give additional and/or altered phenotypic traits is a further aspect of the invention. Such transgenes are often associated with regulatory elements (promoters, enhancers, terminators and the like). As described above, transgenes that can be incorporated into a plant of this invention include, but are not limited to, insect resistance, nematode resistance, herbicide resistance, disease resistance, increased or decreased starch or sugars or oils, lengthened or shortened life cycle or other altered trait, in any combination. In further embodiments, the present invention provides wheat variety R14000248 #58 and progeny thereof expressing at least one transgenic gene useful as a selectable marker or a screenable marker, as are well known in the art.

Genotyping and Genetic Marker Profiles

Several well-known methods can be employed to identify the genotype of a wheat plant. One of the oldest methods is the use of isozymes, which provides a generalized footprint of the genetic material. Other approaches adapted to provide a higher definition profile include restriction fragment length polymorphisms (RFLPs), amplified fragment length polymorphisms (AFLPs), random amplified polymorphic DNAs (RAPDs), amplification methods such as the polymerase chain reaction (PCR), which can employ different types of primers or probes, microsatellites (SSRs), single nucleotide polymorphisms (SNPs), sequence selection markers, etc. as are well known in the art and can be found in standard textbooks such as Breeding Field Crops, Milton et. al. Iowa State University Press and Genetic Mapping and Marker Assisted Selection: Basics, Practice and Benefits, N. Manikanda Boopathi Springer India 2013. Another approach for genotyping includes sequencing methods such as whole genome sequencing, Sanger sequencing, next generation sequencing, shotgun sequencing, exome-capture sequencing, long-read sequencing, pyrosequencing, sequencing by synthesis, SOLiD sequencing, nanopore sequencing, genapsys sequencing, and the like.

The marker profile of the inbred of this invention should be close to homozygous for alleles. A marker profile produced with any of the locus identifying systems known in the industry will identify a particular allele at a particular locus. An F1 hybrid made from the inbred of this invention will comprise a marker profile of the sum of both of the profiles of its inbred parents. At each locus, the allele for the inbred of the present invention and the allele for the other inbred parent should be present. Thus, the profile of the inbred of the present invention allows for identification of hybrids as containing the inbred parent of the present invention. To identify the female portion of any hybrid, the hybrid seed material from the pericarp, which is maternally inherited, may be employed in a marker technique. The resultant profile, therefore, is of the maternal parent. A comparison of this maternal profile with the hybrid profile will allow the identification of the paternal profile. Accordingly, some embodiments of the present invention provide an inbred or hybrid plant, plant part thereof, including but not limited to a seed or an embryo, and/or a cell thereof having the allele marker profile of the inbred plant of this invention.

Marker profiles of plants of this invention can be employed to identify essentially derived varieties or progeny developed with the inbred in its ancestry. The progeny of the inbred line of this invention, can be identified by identifying in the progeny the molecular marker profile of wheat variety R14000248 #58, as measured by either percent identity or percent similarity.

As described herein, marker systems are not just useful for identification of the plants of this invention but can also be used for breeding and trait conversion techniques. Polymorphisms in wheat permit the use of markers for linkage analysis. If SSRs are employed with flanking primers, the marker profile can be developed with PCR, and therefore Southern blots can often be eliminated. Use of flanking markers, PCR and amplification to genotype wheat is well known in the art.

Production of Treated Seed

The present invention encompasses a method of producing treated hybrid or inbred seed of the plants of the present invention and the resultant treated seed. The method includes obtaining seed and treating the seed to improve its performance. Hybrid and inbred seed is often treated with one or more of the following including, but not limited to, fungicides, herbicides, herbicidal safeners, fertilizers, insecticides, acaricides, nematocides, bactericides, virus resistant material and/or other biocontrol agents, e.g., treatments containing one or more of thiamethoxam, mefenoxam, fludioxonil, sedaxane, difenoconazole, metalaxyl-M, such as CRUISERMAXX® VIBRANCE®, CRUISERMAXX® Cereals, and CRUISER® 5FS. Methods for treating seed include but are not limited to the use of a roller mill, a rotostatic seed treater, a drum coaster, misting, soaking, filming coating and the like, in any combination. These methods of seed treatment are well known in the industry.

Wheat as Human Food and Livestock Feed

Wheat may be used to produce a variety of products, including, but not limited to, grain, flour, baked goods, cereals, crackers, pasta, beverages, livestock feed, biofuel, straw, construction materials, and starches. The hard wheat classes are milled into flour used for breads, while the soft wheat classes are milled into flour used for pastries and crackers. Wheat starch is used in the food and paper industries as laundry starches, among other products. The grain of wheat is a staple food in many countries, supplying at least 20% of the food kilojoules for the total world population.

The present invention further encompasses a hybrid plant with a plant part being the segregating grain kernel of the hybrid. This grain is a commodity plant product as are the flour, protein concentrate, protein isolate, or starch. Several different industrial processes can be employed to extract or utilize these plant products, as are well known in the art.

The seed of the plant of the present invention can further comprise one or more additional traits such as single gene traits. The plant produced from the inbred seed of wheat variety R14000248 #58, the hybrid wheat plant produced from the crossing of said inbred, hybrid seed and various parts of the hybrid wheat plant, can be utilized for human food, livestock feed, and as a raw material in industry.

The present invention therefore also provides a commodity plant product, such as an agricultural product or industrial product. In some embodiments, the agricultural product comprises a plant of the present invention or is derived from a plant of the present invention. The present invention further provides an industrial product comprising a plant of the present invention or is derived from a plant of the present invention. Additionally, provided herein are methods of producing an agricultural and/or industrial product, the methods comprising planting seeds of the present invention, growing plant from such seeds, harvesting the plants and/or processing them to obtain an agricultural or industrial product. In some embodiments, the present invention provides a method of producing a commodity plant product comprising growing the plant from the seed of this invention or a part thereof and producing said commodity plant product, wherein said commodity plant product includes, but is not limited to, flour, a protein concentrate, a protein isolate, starch, or starch, or any combination thereof.

DEPOSIT INFORMATION

Applicants have made a deposit of at least 625 seeds of wheat variety R14000248 #58 with the American Type Culture Collection (ATCC) Patent Depository, 10801 University Blvd., Manassas, VA 20110, under the terms of the Budapest Treaty. The ATCC accession number of the deposit is PTA-127507. The date of deposit is Feb. 2, 2023. Access to this deposit will be available during the pendency of the application to the Commissioner for Patents and persons determined by the Commissioner to be entitled thereto upon request. Upon granting of a patent on any claims in the application all restrictions upon availability to the public will be irrevocably removed. The ATCC deposit will be maintained in that depository, which is a public depository, for a period of 30 years, or 5 years after the last request, or for the enforceable life of the patent, whichever is longer, and will be replaced if it becomes nonviable during that period. Applicants do not waive any infringement of its rights granted under this patent or under the Plant Variety Protection Act (7 USC § 2321 et seq.).

EXAMPLES

Example 1: Variety Information

Characteristics and traits of wheat variety R14000248 #58 are shown in the following tables. Tables 2-4 show data for wheat variety R14000248 #58. Tables 5-7 show hybrid data where wheat variety R14000248 #58 was used as one of the parents.

TABLE 1

| Characteristics and Traits of wheat variety R14000248#5 | Value |
|---|---|
| 1. KIND | |
| 1 = common 2 = Durum 3 = Club 4 = Other | 1 |
| 1a. Common Wheat Market Classes HRW, HRS, HW, SRW, SW | HRW |
| 2. VERNALIZATION | |
| 1 = Spring 2 = Winter 3 = Other | 3 |
| 3. COLEOPTILE ANTHOCYANIN | |
| 1 = Absent 2 = Present | N/A |
| 4. JUVENILE PLANT GROWTH | |
| 1 = Prostrate 2 = Semi-Erect 3 = Erect | 2 |
| 5. PLANT COLOR | |
| 1 = Yellow-Green 2 = Green 3 = Blue-Green | 2 |
| 6. FLAG LEAF | |
| 1 = Erect 2 = Recurved | 1 |
| 1 = Not Twisted 2 = Twisted | 2 |
| 1 = Wax Absent 2 = Wax Present | 2 |
| 7. EAR EMERGENCE | |
| Number of Days (Average) | |
| 8. ANTHER COLOR | |
| 1 = Yellow 2 = Purple | 1 |
| 9. PLANT HEIGHT | |
| cm (Average) | |
| 10. STEM | |
| ANTHOCYANIN 1 = Absent 2 = Present | 1 |
| WAXY BLOOM 1 = Absent 2 = Present | 1 |
| HAIRINESS (last internode of rachis) 1 = Absent 2 = Present | 1 |
| INTERNODE 1 = Hollow 2 = Semi-Solid 3 = Solid | 1 |
| Number of Nodes | 5 |
| PEDUNCLE 1 = Erect 2 = Recurved 3 = Semi-Erect | 1 |
| AURICLE Anthocyanin: 1 = Absent 2 = Present | 1 |
| AURICLE Hair: 1 = Absent 2 = Present | 1 |
| 11. HEAD | |
| DENSITY 1 = Lax 2 = Middense (Laxidense) 3 = Dense | 1 |
| SHAPE 1 = Tapering 2 = Strap 3 = Clavate 4 = Other (Specify) | 1 |

TABLE 1-continued

| Characteristics and Traits of wheat variety R14000248#5 | Value |
|---|---|
| CURVATURE 1 = Erect 2 = Inclined 3 = Recurved | 1 |
| AWNEDNESS 1 = Awnless 2 = Apically Awnletted 3 = Awnletted 4 = Awned | 4 |
| 12. GLUMES | |
| COLOR 1 = White 2 = Tan 3 = Other (Specify) | 1 |
| SHOULDER 1 = Wanting 2 = Oblique 3 = Rounded 4 = Square 5 = Elevated 6 = Apiculate 7 = Other (Specify) | 2 |
| SHOULDER WIDTH 1 = Narrow 2 = Medium 3 = Wide | 1 |
| BEAK 1 = Obtuse 2 = Acute 3 = Acuminate | 3 |
| BEAK WIDTH 1 = Narrow 2 = Medium 3 = Wide | 2 |
| LENGTH 1 = Short (ca. 7 mm) 2 = Medium (ca. 8 mm) 3 = Long (ca. 9 mm) | 1 |
| WIDTH 1 = Narrow (ca. 3 mm) 2 = Medium (ca. 3.5 mm) 3 = Wide (ca. 4 mm) | 2 |
| PUBESCENCE 1 = Not Present 2 = Present | 2 |
| 13. SEED | |
| SHAPE 1 = Ovate 2 = Oval 3 = Elliptical | 1 |
| CHEEK 1 = Rounded 2 = Angular | 1 |
| BRUSH 1 = Short 2 = Medium 3 = Long | 2 |
| BRUSH 1 = Not Collared 2 = Collared | 1 |
| CREASE 1 = Width 60% or less of Kernel 2 = Width 80% or less of Kernel 3 = Width Nearly as Wide as Kernel | 2 |
| CREASE 1 = Depth 20% or less of Kernel 2 = Depth 35% or less of Kernel 3 = Depth 50% or less of Kernel | 2 |
| COLOR 1 = White 2 = Amber 3 = Red 4 = Other (Specify) | 3 |
| TEXTURE 1 = Hard 2 = Soft 3 = Other (Specify) | 1 |
| PHENOL REACTION 1 = Ivory 2 = Fawn 3 = Light Brown 4 = Dark Brown 5 = Black | |
| SEED WEIGHT g/1000 Seed (Whole Number Only) | |
| GERM SIZE 1 = Small 2 = Midsize 3 = Large | 2 |

TABLE 2

| Inbred | Yield bu/A | Test Wt. lbs/bu | Heading Julian Date | Height cm. | Winter Hardiness 1-9 |
|---|---|---|---|---|---|
| R14000248#58 | 63.13 | 62.7 | 129 | 77 | 3 |
| SY Monument | 62.95 | 61.9 | 130 | 75 | 3 |
| SY Wolverine | 65.13 | 63.6 | 127 | 72 | 4 |
| No. of Locs. | 6 | 6 | 3 | 2 | 4 |

| Inbred | Aluminum Tolerance | Fusarium Head Blight | BLS | Wheat Streak Mosaic Virus | Stripe Rust |
|---|---|---|---|---|---|
| Scale | 1-9 | 1-9 | 1-9 | 1-9 | 1-9 |
| R14000248#58 | 8 | 5 | 4 | 4 | 4 |
| SY Monument | 2 | 7 | 4 | 8 | 3 |
| SY Wolverine | 8 | 7 | 3 | 4 | 7 |
| No. of Locs. | 4 | 4 | 2 | 3 | 7 |

TABLE 3

| Inbred | Wheat Protein % | Flour Protein % | Flour Hardness | Flour Yield % | Ash % |
|---|---|---|---|---|---|
| R14000248#58 | 13.5 | 11.9 | 150 | 70.9 | 0.5 |
| SY Monument | 12.3 | 11.2 | 165.6 | 69.4 | 0.5 |
| SY Wolverine | 11.7 | 10.6 | 157.7 | 71.9 | 0.5 |
| No. of Locs. | 2 | 2 | 2 | 2 | 2 |

TABLE 4

| | Mixograph Data | | | | |
|---|---|---|---|---|---|
| Inbred | Peak Time min | Peak Height cm | Tol. | Rating 1-9 | Mixo Abs. % |
| R14000248#58 | 3.00 | 5.35 | 959.00 | 5.00 | 61.50 |
| SY Monument | 7.29 | 4.99 | 1330.86 | 3.86 | 61.86 |
| SY Wolverine | 4.45 | 5.08 | 707.60 | 7.30 | 58.60 |
| No. of Locs. | 2 | 2 | 2 | 2 | 2 |

| | Baking Data | | | | | |
|---|---|---|---|---|---|---|
| | Bake | Mix | Loaf | Crumb | | |
| Inbred | Abs. % | Time min | Vol. cc | Grain 1-9 | Text 1-6 | Color 1-6 |
| R14000248#58 | 61.5 | 2.7 | 1150 | 4 | 2 | 3 |
| SY Monument | 62.2 | 4.7 | 975.0 | 3.6 | 2.8 | 2.2 |
| SY Wolverine | 57.8 | 2.9 | 878.3 | 4.7 | 3.7 | 4.3 |
| No. of Locs. | 2 | 2 | 2 | 2 | 2 | 2 |

TABLE 5

| Hybrid or Commercial Name | Yield bu/A | Test Wt. lbs/bu | Heading Julian Date | Height cm. | Winter Hardiness 1-9 |
|---|---|---|---|---|---|
| HCP20300010 | 78.35 | 63.1 | 124 | 61 | 4 |
| SY Monument | 71.09 | 61.4 | 128 | 61 | 3 |
| SY Wolverine | 74.35 | 62.5 | 125 | 56 | 4 |
| No. of Locs. | 15 | 14 | 3 | 2 | 4 |

| Hybrid or Commercial Name | Aluminum Tolerance 1-9 | Fusarium Head Blight 1-9 | BLS 1-9 | Wheat Streak Mosaic Virus 1-9 | Stripe Rust 1-9 |
|---|---|---|---|---|---|
| HCP20300010 | 4 | 7 | 3 | 3 | 7 |
| SY Monument | 2 | 7 | 4 | 8 | 3 |
| SY Wolverine | 8 | 7 | 3 | 4 | 7 |
| No. of Locs. | 4 | 4 | 2 | 3 | 7 |

TABLE 6

| Hybrid or Commercial Name | Wheat Protein % | Flour Protein % | Flour Hardness | Flour Yield % | Ash % |
|---|---|---|---|---|---|
| HCP20300010 | 12.5 | 11.4 | 167.7 | 71.4 | 0.4 |
| SY Monument | 12.3 | 11.2 | 165.6 | 69.4 | 0.5 |
| SY Wolverine | 11.7 | 10.6 | 157.7 | 71.9 | 0.5 |
| No. of Locs. | 2 | 2 | 2 | 2 | 2 |

TABLE 7

| | Mixograph Data | | | | |
|---|---|---|---|---|---|
| Hybrid or Commercial Name | Peak Time min | Peak Height cm | Tol. | Rating 1-9 | Mixo Abs. % |
| HCP20300010 | 4.50 | 5.17 | 913.33 | 5.17 | 61.17 |
| SY Monument | 7.29 | 4.99 | 1330.86 | 3.86 | 61.86 |
| SY Wolverine | 4.45 | 5.08 | 707.60 | 7.30 | 58.60 |
| No. of Locs. | 2 | 2 | 2 | 2 | 2 |

TABLE 8

| | Baking Data | | | | | |
|---|---|---|---|---|---|---|
| Hybrid or | Bake | Mix | Loaf | Crumb | | |
| Commercial Name | Abs. % | Time min | Vol. cc | Grain 1-9 | Text 1-6 | Color 1-6 |
| HCP20300010 | 61.2 | 3.2 | 1001.7 | 4.2 | 2.7 | 3.3 |
| SY Monument | 62.2 | 4.7 | 975.0 | 3.6 | 2.8 | 2.2 |
| SY Wolverine | 57.8 | 2.9 | 878.3 | 4.7 | 3.7 | 4.3 |
| No. of Locs. | 2 | 2 | 2 | 2 | 2 | 2 |

Accordingly, the present invention has been described with some degree of particularity directed to the embodiment of the present invention. It should be appreciated, though that the present invention is defined by the following claims construed in light of the prior art so that modifications or changes may be made to the embodiment of the present invention without departing from the inventive concepts contained herein.

What is claimed is:

1. A seed of wheat line R14000248 #58, wherein representative seed of said wheat line R14000248 #58 has been deposited under ATCC Accession Number PTA-127507.

2. A plant of wheat line R14000248 #58, wherein representative seed of said wheat line R14000248 #58 has been deposited under ATCC Accession Number PTA-127507.

3. A plant part of the plant of claim 2.

4. A seed produced on the plant of claim 2.

5. A process for producing wheat seed, said process comprising crossing wheat line R14000248 #58 with a different wheat plant, and harvesting the seed, wherein representative seed of said wheat line R14000248 #58 has been deposited under ATCC Accession Number PTA-127507.

6. A method of producing a genetic marker profile comprising extracting nucleic acids from the seed of claim 1 or the plant germinated from said seed and genotyping said nucleic acids at one or more genetic loci, thereby producing a genetic marker profile.

7. A method of plant breeding comprising a) isolating nucleic acids from the seed of claim 1 or a plant germinated from said seed, b) identifying one or more polymorphisms from the isolated nucleic acids, and c) selecting said seed or a plant obtained from said seed having said one or more polymorphisms, wherein the seed or plant is used in a plant breeding method.

8. A process of introducing an additional trait into a wheat plant comprising: (a) crossing the plant of claim 2 with a plant of another wheat variety that comprises an additional trait to produce hybrid progeny plants, (b) selecting one or more hybrid progeny plants that have the additional trait to produce selected hybrid progeny plant(s); (c) crossing the selected progeny plant(s) with said plant of wheat line R14000248 #58 to produce backcross progeny plants; (d) selecting for one or more backcross progeny plants that have the additional trait to produce selected backcross progeny plant(s); and (e) repeating steps (c) and (d) a sufficient number of times to produce one or more backcross progeny plants that comprise the additional trait and all of the physiological and morphological characteristics of said plant of wheat line R14000248 #58 when grown in the same environmental conditions.

9. A plant produced by the process of claim 8.

10. A method for developing a second wheat variety in a wheat plant breeding program, comprising applying plant breeding techniques wherein said techniques comprise recurrent selection, backcrossing, pedigree breeding, marker enhanced selection, haploid/double haploid production, or transformation to the wheat plant of claim 2, wherein application of said techniques results in development of a second wheat variety.

* * * * *